United States Patent [19]

Bascomb

[11] Patent Number: 4,603,108

[45] Date of Patent: Jul. 29, 1986

[54] METHOD FOR IDENTIFICATION OF BACTERIAL SPECIES

[75] Inventor: Shoshana Bascomb, Reading, England

[73] Assignee: National Research Development Corp., London, England

[21] Appl. No.: 439,877

[22] Filed: Nov. 8, 1982

Related U.S. Application Data

[63] Continuation of Ser. No. 227,048, Dec. 29, 1980, abandoned.

[30] Foreign Application Priority Data

May 2, 1979 [GB] United Kingdom ................ 7915318

[51] Int. Cl.$^4$ ............................................. C12Q 1/04
[52] U.S. Cl. ...................................... 435/34; 435/12; 435/14; 435/16; 435/19; 435/21; 435/24; 435/25; 435/291; 435/810
[58] Field of Search ....................... 435/14, 16, 18, 24, 435/34, 36, 37, 38, 805, 291, 4, 12, 19, 21, 25, 810

[56] References Cited

U.S. PATENT DOCUMENTS

| | | | |
|---|---|---|---|
| 3,451,893 | 6/1969 | Sanders | 435/21 |
| 3,870,601 | 3/1975 | Warren et al. | 435/38 |
| 3,936,356 | 2/1976 | Janin | 435/38 |
| 3,957,584 | 5/1976 | Kronish | 435/38 |

*Primary Examiner*—Sam Rosen
*Assistant Examiner*—William J. Herald
*Attorney, Agent, or Firm*—Oblon, Fisher, Spivak, McClelland & Maier

[57] ABSTRACT

A method for identifying specific bacterial species in derived samples is based on 26 tests for the presence of constitutive enzymes, which, with the exception of two tests which require about two and a half hours, can be done relatively quickly, and without need for bacterial growth. By quantifying the amount of enzyme identified by the substrate test, a highly reliable identification of bacterial species present can be made. A kit, comprising substrates specific to the enzymes to be tested for, is provided for carrying out the test.

11 Claims, 7 Drawing Figures

METHOD FOR IDENTIFICATION OF BACTERIAL SPECIES

This is a continuation of U.S. patent application Ser. No. 227,048, filed Dec. 29, 1980, now abandoned.

This invention relates to the identification of bacteria.

Clinical bacteriology laboratories are frequently called upon to test for the presence of pathogenic bacteria in clinical specimens and further to identify the type of bacteria concerned to help guide the clinician in the choice of treatment, e.g. antibiotic, which is to be used to combat infection.

Customary bacterial identification procedures rely upon a series of characterisation tests on the basis of which the unknown organism is assigned to a defined group of bacteria. These tests include tests in which bacteria are classified by their ability to metabolise various substrates, metabolism being determined by resultant changes in the substrate media, e.g. pH changes, which may be detected by use of coloured indicators. For such metabolic tests it is necessary, however, to grow the bacteria, usually in complete growth media, and this requires considerable expenditure of time so that it is rarely possible to identify the bacteria on the same day as the specimen arrives in the laboratory. Often, if conventional bacteria identification procedures are used, definitive identification is not possible until 48-72 hours after receipt of the specimen. In the meantime, the treatment prescribed by the clinician can at best be only a guess and may be initially incorrect, with the consequence that the infection persists and the condition of the patient deteriorates. There is a pressing need, therefore, for increase in the speed of identification of bacteria which cause infections so that the correct treatment, e.g. antibiotic, may be prescribed without undesirable delay.

Very recently bacterial identification procedures have been proposed which rely only to a limited extent upon bacterial growth for identification, but depend more upon determination of enzymes which are initially present in the bacteria or are induced after a relatively short period of time, e.g. a few hours, and these tests enable bacterial identification to be made earlier than previously, sometimes on the same day as receipt of the sample. Each of these bacterial identification procedures, however, generally permits identification only of bacteria within certain limited groups and it is thus necessary to carry out a preliminary identification, usually requiring bacterial growth, to select the particular identification procedure which should be used.

A new bacterial identification procedure has now been devised which relies purely upon determination of enzymes present within the organisms, and additionally advantageously provides a single identification procedure by which a very wide range of commonly encountered bacteria may be identified very rapidly.

Accordingly the present invention comprises a procedure for the identification of bacteria, in which bacteria are subjected to a combination of tests for determination of:
(a) lipase
(b) α-glucosidase
(c) β-glucosidase
(d) β-xylosidase
(e) β-glucuronidase
(f) β-galactosidase
(g) whole cell acid phosphatase
(h) acid phosphatase in the presence of agents which disrupt the bacterial cell permeability barrier
(i) D L-alanyl-β-naphthylamine specific peptidase
(j) L-arginyl-β-naphthylamine specific peptidase
(k) N-γ-L-glutamyl-β-naphthylamine specific peptidase
(l) glycyl-β-naphthylamine specific peptidase
(m) L-4-hydroxyprolyl-β-naphthylamine specific peptidase
(n) L-leucyl-β-naphthylamine specific peptidase
(o) L-leucyl-4-methoxy-β-naphthylamine specific peptidase
(p) L-lysyl-β-naphthylamine specific peptidase
(q) L-prolyl-β-naphthylamine specific peptidase
(r) L-pyrrolidonyl-β-naphthylamine specific peptidase
(s) alanyl-p-nitroaniline specific peptidase
(t) glutamyl-p-nitroaniline specific peptidase
(u) diacetyl/acetoin producing enzymes
(v) p-nitrophenylalanine ammonia-lyase
(w) tryptophanase
(x) deoxyribonuclease
(y) glutamate decarboxylase
(z) cytochrome oxidase The procedure of the invention may be used for identification of a very wide range of bacteria, including most of those bacteria which are customarily encountered clinically. In particular, the procedure may be used to identify the commonly encountered bacterial groups: Aeromonas, Acinetobacter, Alcaligenes, Bordatella, Citrobacter, Edwardsiella, Enterobacter, Escherichia, Flavobacterium, Hafnia, Klebsiella, Providencia, Proteus, Pseudomonas, Salmonella, Serratia, Shigella, Staphylococcus and Streptococcus. For example the procedure of the invention has been used to identify the following bacterial species:

*Aeromonas hydrophila*
*Aeromonas formicans*
*Acinetobacter calcoaceticus* var. *anitratus*
*Acinetobacter calcoaceticus* var. *lwoffii*
*Alcaligenes faecalis*
*Bordatella bronchiseptica*
*Citrobacter freundii*
*Citrobacter koseri*
*Edwardsiella tarda*
*Enterobacter aerogenes*
*Enterobacter agglomerans*
*Enterobacter cloacae*
*Escherichia coli*
*Flavobacterium meningosepticum*
*Hafnia alvei*
*Klebsiella oxytoca*
*Klebsiella pneumoniae* (*sensu lato*)
*Klebsiella rhinoscleromatis*
*Providencia alcalifaciens*
*Providencia stuartii*
*Proteus mirabilis*
*Proteus morganii*
*Proteus rettgeri*
*Proteus vulgaris*
*Pseudomonas aeruginosa*
*Pseudomonas cepacia*
*Pseudomonas fluorescens*
*Serratia marescens*
*Serratia rubidaea*
*Serratia liquefaciens*
*Staphylococcus aureus*
*Staphylococcus epidermidis*
*Staphylococcus saprophyticus*
*Streptococcus sp*

It will be appreciated, however, that the procedure of the invention may also be applied to the identification of other bacterial species besides those listed above.

The procedure of the invention permits very rapid identification of bacteria, the enzyme determination tests used generally requiring only a relatively short period of incubation, e.g. from about 10 minutes up to about 2 hours, usually from about 30 to about 90 minutes at about 40° C., to give sufficient product for detection e.g. by spectroscopic measurements. It is believed that generally the enzymes which are determined during the procedure of the invention are constitutive enzymes for the bacteria concerned, though in two cases referred to below the enzymes may be induced enzymes the rates of bacterial synthesis of which are very fast. Thus the tests used are generally those suitably adapted for determination of constitutive enzymes. Without prejudice to the foregoing, however, determination of tryptophanase and deoxyribonuclease appears to require bacterial growth, usually requiring incubation for a period of 2-2½ hours.

Generally the tests which are used in the procedure of the invention for determination of bacterial enzymes may comprise any suitable tests for the determination of the enzymes in question which are characteristically not dependent on growth of the organisms during the test, and which may include those non-growth enzyme determination tests for the enzymes in question which are well known in the art.

These tests are usually of the kind in which the enzyme is determined by its ability to interact with a specific substrate. Interaction of the enzyme with the substrate, on incubation, usually gives rise to a product which may be detected either directly or after further treatment which may include chemical synthesis from the initial enzyme product.

The product of the enzyme interaction is determined, e.g. by spectrometric measurements including fluorimetry or colorimetry. For example, the specific enzyme substrate may comprise an umbelliferyl derivative which on interaction with the enzyme gives rise to umbelliferone which is monitored fluorimetrically, or the substrate may comprise a nitrophenyl, nitroaniline or similar type of derivative which on interaction with the enzyme gives rise to a coloured product which is monitored colorimetrically.

An example of an enzyme which may be determined by spectrometric measurement of the direct product of enzyme interaction with a substrate is cytochrome oxidase; for instance, by interaction of sample with tetramethyl-p-phenylene-diamine (TMPD) an indicator which is oxidised by cytochrome oxidase to give a purple colouration. Also acid phosphatases, betagalactosidases and phenylalanine deaminases may be determined spectrometrically; for instance, using nitrophenyl derivatives, though it is normally necessary to treat the enzyme-substrate mixture with alkali subsequent to incubation so as to develop the nitrophenol coloration by raising the pH above the pH optimum of the enzyme reaction.

Products which require further treatment after enzyme reaction with the substrate before monitoring, may be detected spectrometrically. For example, ammonia-releasing enzymes, such as leucine deaminase may be determined by reacting the ammonia produced by the enzyme interaction with a color-producing reagent such as the Nessler reagent, and monitoring the resultant colour by colorimetric measurement. The ammonia released may be measured directly in the enzyme-substrate reaction mixture or may be removed, e.g. by dialysis, from the reaction mixture before assay.

Also, for example, diacetyl producing or acetoin producing enzymes may be determined by spectrometric monitoring of enzyme products after further treatment. Such enzymes are determined by the Voges-Proskauer technique for testing for the presence of diacetyl/acetoin.

Furthermore, glutamate decarboxylase activity may be determined by colorimetrically determining the carbon dioxide released as a result of interaction of the enzyme with glutamic acid. For instance, carbon dioxide is determined colorimetrically by dialysis out of the reaction mixture after addition of acid, e.g. $H_2SO_4$, through a hydrophobic membrane into a buffered indicator which changes colour as a result of the change in acidity due to the $CO_2$.

Other enzymes may be determined by suitable techniques; for instance, substrate specific peptidases are determined by use of naphthylamine or nitroaniline derivatives, naphthylamine produced being determined either directly by fluorimetry or by colorimetry after diazonium coupling.

The tests used for determination of the enzymes may be varied as desired, for instance to increase the organism specific selectivity of the tests. Thus, two tests for determination of phosphatase activity are included within the procedure of the invention, one for whole cell acid phosphatase activity and one for acid phosphatase activity in the presence of agents which disrupt the bacterial cell permeability barrier. Any suitable agent may be used, though Cetrimide (cetyltrimethylammonium bromide) and lysozyme, especially in combination, are particularly preferred. The use of such an agent, for instance, has the effect of selectively decreasing the acid phosphatase activity of cells of Proteus bacteria and increasing that of Klebsiella cells.

The invention includes kits of reagents for use in the procedure of the invention. Such kits typically comprise separate specific substrates for each of the enzymes which it is desired to determine in the procedure of the invention. Thus, for example, a basic kit for use in the procedure of the present invention comprises separate specific substrates, for determination of (a)-(z) listed previously. Preferably these substrates are such as to give chromogenic or fluorogenic products on interaction with corresponding enzymes to advantageously permit colorimetric or fluorimetric monitoring. Additionally the kits may also comprise suitable buffer solutions and other reagents, e.g. colour-developing or fluorescence-developing reagents.

The procedure of the present invention is generally applicable to the identification of bacteria in clinical specimens including urine samples, throat swabs and sputum, wound swabs, stools and blood samples. Bacteria may be isolated from the specimens prior to identification. For example, bacterial cultures are prepared from the specimens and colonies of the organisms to be identified are harvested from the cultures after a sufficient period of growth, e.g. normally about 18 hours, and made up into a suitable form, e.g. suspension form, for determination by the procedure of the invention. In particularly preferred embodiments, however, it is envisaged that the procedure of the invention will be carried out on samples derived directly from clinical specimens, for instance, on samples derived directly from urine samples, without need for growth of bacteria and isolation of single colonies.

Prior to assay of bacterial enzymes, however, the samples containing bacteria, whether derived directly from clinical specimens or derived as single colonies after bacterial growth, may in some cases be subjected to treatment to disrupt the permeability barrier of the bacteria and release the enzymes for assay. Any suitable treatment may be used to disrupt the bacterial permeability barrier. Generally during determination of cytoplasmic and periplasmic enzymes, such as $\beta$-galactosidases and acid phosphatases, such prior disruption of the bacterial permeability barrier may be desirable, though other enzymes, such as deaminases, which appear to be membrane-associated may require the bacterial cells to be kept intact for enzyme activity to be maintained.

The enzyme assay tests of the procedure of the invention may be carried out by any suitable method or means, including continuous flow and discrete sample analysis techniques, such as those which are well known in the art. In one embodiment a discrete analyser, such as the Kem-O-Mat system, is used. In another embodiment the enzymes may be assayed by automated continuous flow analysis techniques. In such continuous flow analysis methods it may be desirable to include a protein determination in view of the differing protein concentrations of various bacteria, so that the enzyme specific activities of the bacteria may be determined. Also a protein assay may provide a measure of the blank in spectrometric assays for the absorbance due to the concentration of the organisms.

The conditions used during enzyme determinations may be varied as desired. For example, in continuous flow analysis techniques the relative organism to reagent concentration may be raised, e.g. a sample to reagent ratio in the range from about 1:3 up to about 3:1, to increase the levels of product formed on interaction of enzyme and substrate and thus permit detection of enzyme at lower bacterial suspension concentrations. Also, preferably, relatively elevated temperatures, e.g. temperatures of about 40° C., may be used during incubation of sample and substrate to increase the rate of interaction. Preferably, using continuous flow techniques, it is possible to achieve bacterial identification at a very early stage, especially within about 1 hour of the sample reaching the laboratory e.g. if apparatus comprising a single channel for each enzyme test is employed.

In further preferred embodiments, however, the procedure of the invention may be carried out using a test card or other suitable apparatus comprising a plurality of wells or compartments which separately contain specific enzyme substrates for each of the enzyme tests of the procedure and comprising other reagents, as required, e.g. colour-developing reagents. In use, the sample, usually bacterial suspension, is added to each compartment and a detectable product is developed after a relatively short incubation period e.g. from about 20 minutes up to about 2 hours in preferred embodiments. The amount of the corresponding enzymes present in the bacterial sample is then determined. Such apparatus is included within the scope of the invention, and in particularly preferred embodiments may be adapted to handling by automated techniques including automated, preferably computerised, spectrometric scanning techniques which identify the bacterial species directly from the responses of the enzyme tests.

The procedure of the invention may incorporate additional tests for determination of bacterial enzymes besides those mentioned previously as tests (a)–(z); for instance to strengthen the identification of certain groups of bacteria. Thus, the procedure may include a test for determination of bacterial urease activity.

In a second aspect the invention also includes a bacterial identification procedure for use in the rapid differentation of the commonly encountered bacterial groups Escherichia, Klebsiella spp, Proteus spp and Pseudomonas spp, in which a sample comprising bacteria of one of these groups is subjected to a combination of tests for determination of bacterial acid phosphatase, beta-galactosidase, glutamate decarboxylase, phenylalanine deaminase, cytochrome oxidase, diacetyl/acetoin producing enzymes and urease. This limited combination of seven tests may be used to rapidly differentiate the bacterial groups Escherichia, Klebsiella spp, Proteus spp and Pseudomonas spp substantially as hereinbefore described with reference to the full identification procedure incorporating the 26 tests (a)–(z).

The invention also includes kits for use in this 7 test procedure; the basic kit typically comprising separately specific substrates for acid phosphatase, diacetyl/acetoin-producing enzymes, beta-galactosidase, glutamate decarboxylase, phenylalanine deaminase, cytochrome oxidase and urease activity.

In general the procedures of the invention rely upon determination of the enzyme activity profiles of the bacteria undergoing identification, and in accordance with the invention the combination of enzyme tests chosen, i.e. tests (a)–(z) or the limited combination of 7 tests, typically gives a unique "fingerprint" for the bacteria. The unique "fingerprint" for each species or group of bacteria may be determined with reference to the enzyme activity profiles of previously identified bacteria; for instance, from bacteria obtained from culture collections. Enzyme activity profiles are determined quantitatively. The use of data-processing techniques are desirable to facilitate the identification by comparison of enzyme profiles of unknown bacteria with those of previously identified bacteria. For example, processing of results obtained by discriminant function analysis, e.g. using the SPSS package (Statistical Package for Social Sciences) has been found to be particularly useful.

The procedures of the invention typically permit very rapid identification of bacteria, a single procedure only being required for identification of a very wide range of bacteria, including most of those bacteria which are commonly encountered clinically. This provision of a single procedure advantageously obviates the need for a preliminary test and the undesirable delay that this causes.

The invention is further described by way of illustration only in the following description and examples which refer to the accompanying drawings.

Figure 4:
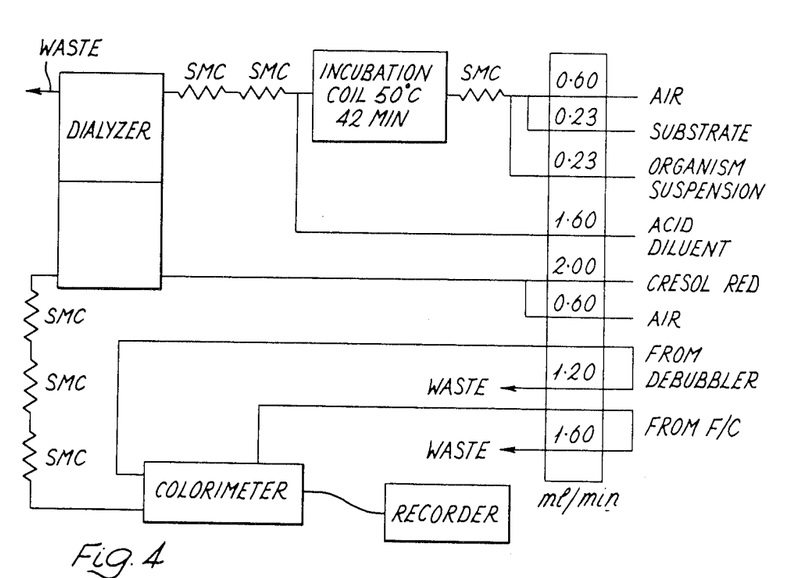
FIG. 4 which is a diagrammatic representation of a similar manifold for analysis of glutamate decarboxylase.
Figure 5:
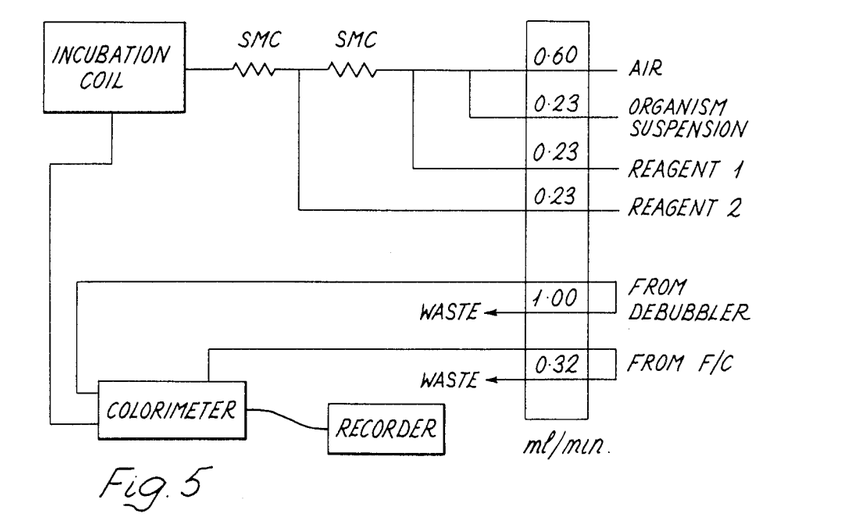
FIG. 5 which is a diagrammatic representation of a similar manifold for assay of cytochrome oxidase and protein.
Figure 6:
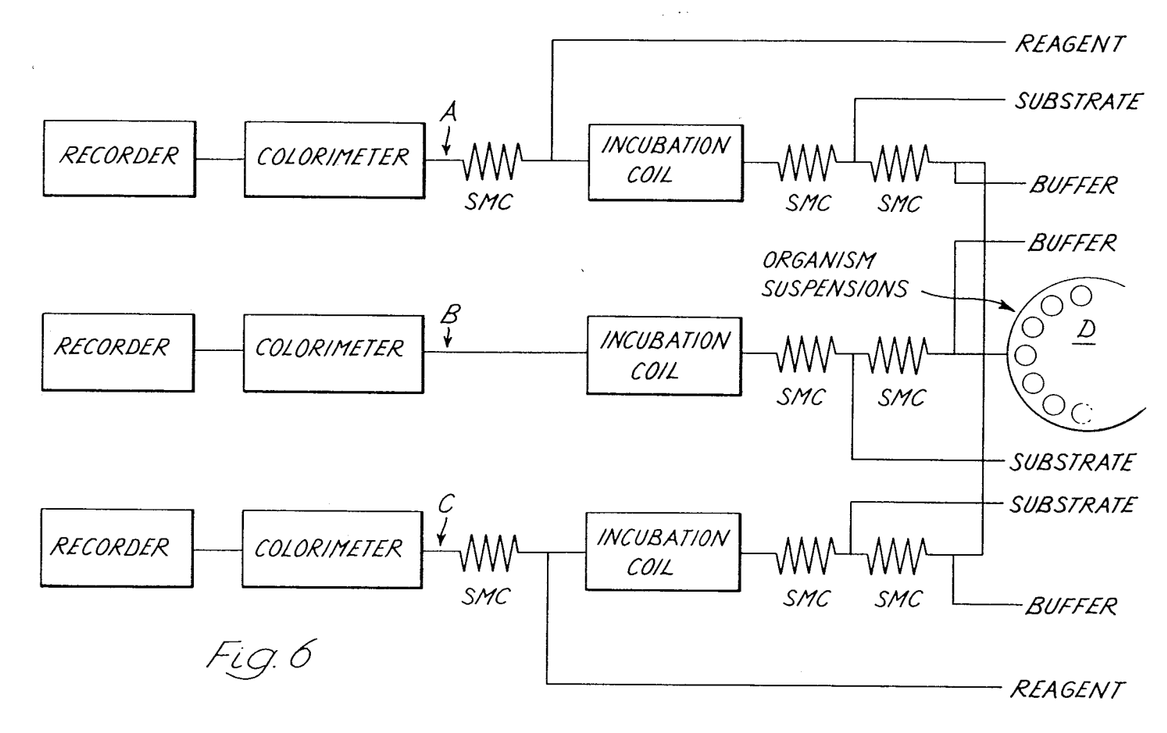
FIG. 6 which is a diagrammatic representation of a flow chart for a three-channel combination continuous flow analysis system for carrying out the procedure of the invention and comprising the manifolds of FIGS. 1 to 5, and FIG. 7 which is a diagrammatic representation of a maifold used for continuous flow analysis of enzymes using substrates which release fluorescently active products.

Tests for determination of bacterial acid phosphatase, beta-galactosidase, glutamate decarboxylase, leucine deaminase, phenylalanine deaminase, cytochrome oxidase, urease and diacetyl/acetoin-producing enzymes are carried out by continuous flow analysis techniques using a three-channel combined system, a flow chart for which is given in FIG. 6, comprising enzyme determination manifolds as shown diagrammatically in FIGS. 1 to 5.

The various enzyme determinations are carried out as follows: Enzymes utilizing nitrophenyl substrates (beta-galactosidase, phenylalanine deaminase and acid phosphatase).

Figure 1:
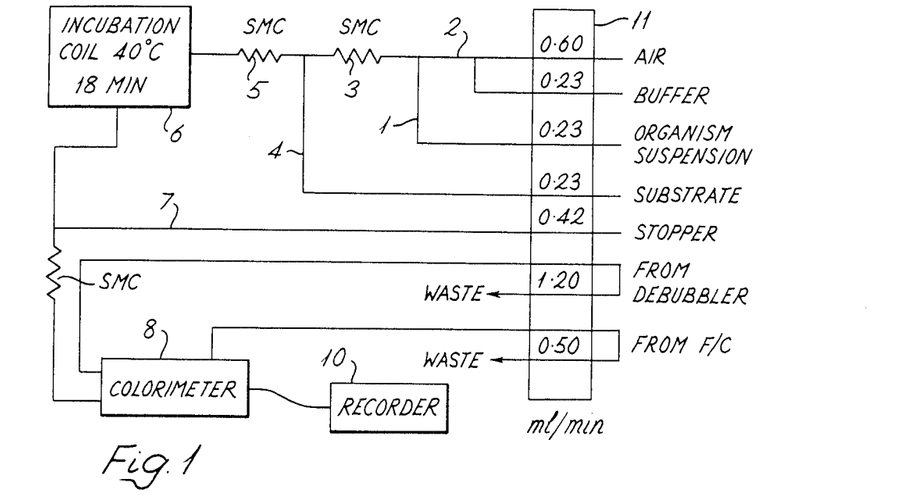
FIG. 1 which is a diagrammatic representation of a manifold used for continuous flow analysis of nitrophenol-releasing enzymes in the procedure of the invention.

The manifold shown in FIG. 1 is used for determination of enzymes utilising nitrophenyl substrates, i.e. beta-galactosidase, phenylalanine deaminase and acid phosphatase.

A stream of organism suspension 1 is mixed with an air-segmented buffer stream 2 in the first single mixing coil (SMC) 3, and is then mixed with the substrate stream 4 in the second SMC 5 and incubated for 18 minutes in a glass coil maintained in an oil bath 6 at 40° C. The reaction is stopped by addition of a strong alkaline solution 7 (1.9M $NH_4OH$, 0.68M NaOH, Triton-X-100 0.3 g/l) which also acts as a colour developer for the released p-nitrophenyl molecule. The stream is then de-bubbled and passed through a 20 mm flow-cell in a photometer 8 and the absorbance measured at 405 nm for beta-galactosidase and acid phosphatase and at 480 nm for phenylalanine deaminase. The absorbance readings obtained are registered on a recorder 10. The figures given in the enclosed area 11 in FIG. 1 are the flow rates used for the various reagent and reactant streams.

The various buffer solutions and substrates used are given below in Table 1.

TABLE 1

Enzyme systems tested with nitrophenyl substrates

| Enzyme | Substrate | Buffer Ion | pH | Additions |
|---|---|---|---|---|
| Acid phosphatase | p-nitrophenyl-phosphate 1.5 mM | 0.1 M Na acetate | 5.6 | 200 µg/ml of cetrimide and lysozyme |
| β-galactosidase | p-nitrophenyl-β-D-galacto-pyranoside 0.5 mM | 0.1 M K phosphate | 7.4 | 200 µg/ml of cetrimide and lysozyme |
| Phenylalanine deaminase | DL-β-(p-nitrophenyl)-alanine 0.5 mM | 0.1 M K phosphate | 8.0 | None |

It is believed that the interaction of phenylalanine deaminase with the DL-β-(p-nitrophenyl)-alanine substrate gives rise to production of p-nitrophenylpyruvic acid which is the product which is measured by absorbance at 480 nm.

Ammonia-releasing enzymes (leucine deaminase and urease)

Figure 2:
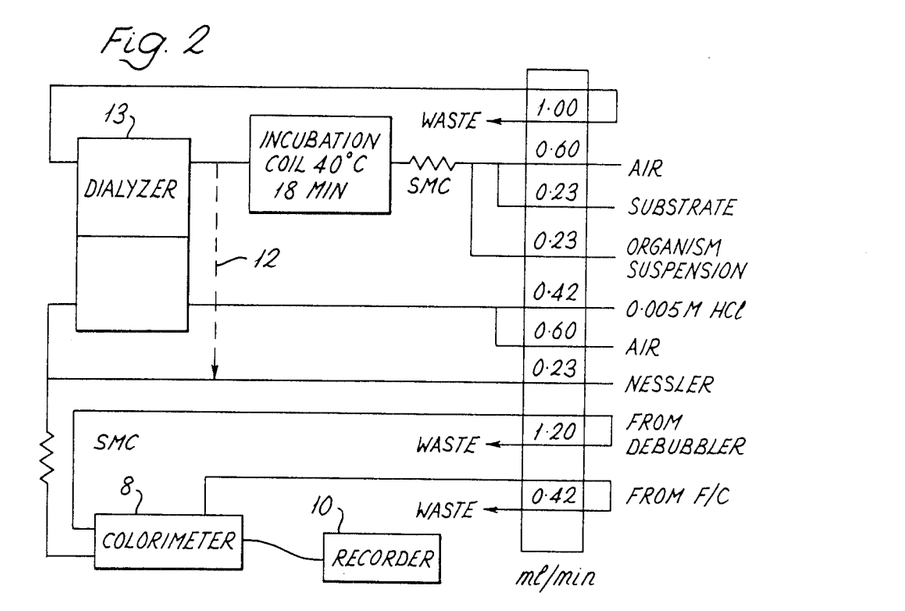
FIG. 2 which is a diagrammatic representation of a similar manifold for analysis of ammonia-releasing enzymes.

With reference to FIG. 2 the method used for assay of ammonia-releasing enzymes, i.e. leucine deaminase and urease, is based on that of Bascomb and Grantham (1975 "Some Methods for Microbiological Assay" ed. Board & Lovelock pp 20–54, Academic Press, N.Y.) but using different sized tubes. Ammonia released from the substrates is assayed by adding the Nessler reagent to ammonia which has been collected by dialysis into a 0.005 MHCl recipient stream. Attempts to measure the ammonia directly in the organism/substrate stream are not satisfactory due to troublesome base-line drift and non-reproducibility of the standards. Urease activity is determined in the absence of Tris, maleate or phosphate buffer as their presence caused a noisy base-line, the enzyme being measured in the presence of distilled water only (pH approximately 4.7–5.0). $NH_4Cl$ solutions are used as standards in both assays. The substrates used are 5 mM L-leucine in 0.5M phosphate borate, pH 8.0 and 100 mM urea in fresh distilled water. The Nessler reagent is prepared as described by Bascomb and Grantham in the above-mentioned publication and diluted 1:10 in fresh glass distilled water daily. A 20 mm flow cell is used in the photometer and absorbance is measured at 420 nm.

In FIG. 2 the functions of the various components and the relevance of the information given is similar to FIG. 1. The broken line arrow 12 indicates the direction of flow by-passing the dialyzer 13 without dialysis.

Diacetyl/acetoin-producing enzymes

Figure 3:
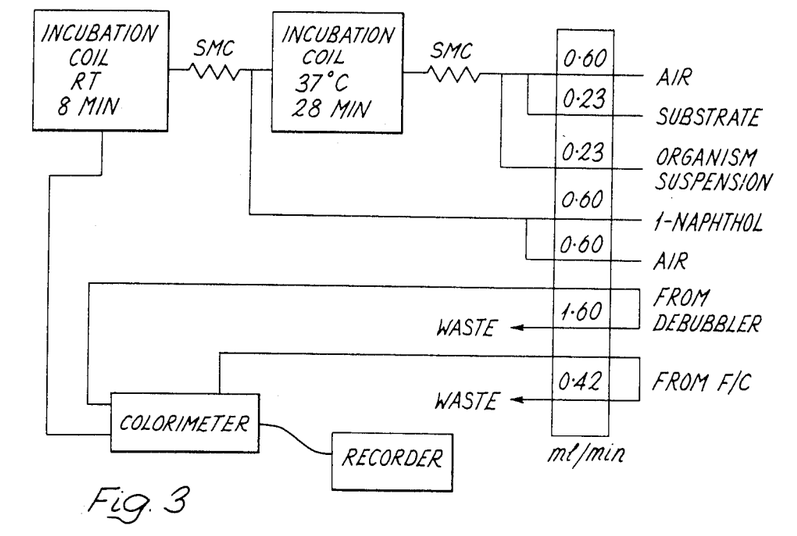
FIG. 3 which is a diagrammatic representation of a similar manifold for analysis of diacetyl/acetoin-producing enzymes.

The Voges-Proskauer reaction for the presence of acetoin/diacetyl is used, in the manifold illustrated in FIG. 3, for determination of diacetyl/acetoin-producing enzymes. The method of measurement used is developed from that described by Kamoun et al. (Clin. Chem. 1972, 18, 355–357). The substrate solution contains 0.3M sodium pyruvate, 0.1M acetate buffer (pH 4.5), 0.1 mM thiamine pyrophosphate and creatine 2 g/l. The 1-naphthol colour-developing reagent is dissolved (25 g/l) in 2M sodium hydroxide. Diacetyl solutions are used as standards. Absorbance is measured at 420 nm using a 20 mm flow cell.

Glutamate decarboxylase

Glutamate decarboxylase is determined, with reference to FIG. 4, by interaction with substrate comprising glutamate to produce $CO_2$ which is dialysed from the reaction mixture into a buffered cresol red solution where its presence causes a colour change in the indicator. The method used is based on those described by Leclerc (Annls. Inst. Pasteur, Paris (1967) 112, 713–731). Moran and Wittler (1976 J. Food Sci. 41, 165–167) and Technicon Methodology AA 11-08. Technicon sodium carbonate standards are used. The substrate used comprises 0.1 M acetate buffer (pH 3.8), 0.05M sodium glutamate and pyridoxal phosphate 20 mg/l. After incubation of the sample and substrate 0.5M sulphuric acid diluent, containing Brij-35 (30% Technicon) 1 ml/l, is added to lower the pH and assist removal of $CO_2$ produced by dialysis through a hydrophobic dialysis membrane. The colour reagent used contains 0.4 mM Tris, ammonia solution 28 µl/l, Brij-35 20 µl/l cresol red 20 µg/l. Absorbance is measured at 420 nm in a 10 mm flow cell.

Cytochrome Oxidase and Protein Assays

Cytochrome oxidase and protein are assayed using the manifold apparatus illustrated in FIG. 5—which contains similar information and components having similar functions as in FIGS. 1 to 4.

The reagents used for assay of cytochrome oxidase activity are 0.05M Tris-maleate buffer, pH 6.0, introduced prior to the first single mixing coil, 0.5 mM N,N,N'N'-tetramethyl-p-phenylene diamine dihydrochloride in 0.001% (w/v) ascorbic acid introduced prior to the second single mixing coil. The incubation period used is 17 minutes at room temperature and absorption is measured at 550 nm in a 10 mm flow cell.

Protein assay

The protein assay used is based on that of Lowry et al (1951, J. Biol. Chem., 193, 265–275) and as described by Bascomb and Grantham in the above-mentioned publication, though using smaller tubes. The reagents used are alkaline copper solution prepared daily by mixing two ml sodium potassium tartrate (10 g/l) with 2 ml $CuSO_4.5H_2O$ (5 g/l) and 46 ml 0.2M NaOH containing 0.37M $Na_2CO_3$ (anhydrous), in the order described. The alkaline copper reagent is introduced prior to the first single mixing coil. Folin-ciocalteu's reagent (BDH) is diluted 1:8 in distilled water daily and introduced prior to the second single mixing coil. The incubation period used is 17 minutes at room temperature and absorption is measured at 660 nm in a 10 mm flow cell. Bovine serum albumin solutions are used as standards. A few drops of chloroform are added to the sodium tartrate, carbonate and protein standard solutions to prevent microbial contamination.

The enzyme assays described above are carried out in a combined continuous flow analysis system, the flow chart of which is illustrated in FIG. 6, comprising three channels which are run simultaneously: one channel (A) for assaying enzymes utilising nitrophenyl derivatives, the second channel (B) for assaying protein and cytochrome oxidase, and the third channel (C) for assaying diacetyl/acetoin producing, ammonia-producing and $CO_2$-producing (glutamate decarboxylase) enzymes. The $NH_3$ and $CO_2$ products are dialysed from the reaction mixtures and the Nessler and 1-naphthol colour-developing reagents added, where appropriate, between the incubation coil and the third SMC. The stream from the single sample probe is divided into three, providing bacterial suspensions to each of the channels A, B and C. The bacterial suspensions are maintained in cups on a revolving sample plate D, while substrates and buffer solutions are provided in continuous streams via the tubes.

All bacterial suspensions are first tested for activity of three enzymes, one in each of the channels A, B and C. When the cycle is complete, the substrate, buffer and sample lines are transferred manually to reagents for the next batch of three tests and the sampling of bacteria is restarted. This process is repeated four times, including control runs with distilled water in the substrate lines to obtain the absorbance values of bacterial suspensions in the acid phosphatase, cytochrome oxidase, leucine deaminase and urease assays.

EXAMPLE 1

A total of 199 suspensions of different bacteria are tested by the procedure outlined above using the continuous flow apparatus illustrated in the accompanying drawings. The bacteria are isolated from routine urine specimens cultured overnight at 37° C. on MacConkey agar plates (Difco Laboratories or Tissue Culture Services). Only plates that show a homogeneous colony appearance are used.

Bacterial suspensions each comprising ten colonies in 5 ml saline are prepared in a separate location and are brought to the automated system to ensure that automated identification is carried out without any knowledge of the colonial appearance of the samples. A 0.1 ml aliquot is removed from each suspension and added to 5 ml nutrient broth which is then incubated at 37° C. for 2 hours on a Matburn rotary mixer. These suspensions are used for inoculation of a chosen set of conventional test media and a nutrient agar slope to be kept for further testing. The remaining saline suspension is tested directly by the automated procedure. Cetrimide and lysozyme and included in the buffer solutions for acid phosphatase and $\beta$-galactosidase assays and mixed with the saline organism suspensions for 2½ minutes at room temperature prior to addition of the substrate to effect disruption of the bacterial permeability barrier. This treatment halved the absorbance at 340 nm of all gram-negative bacteria tested.

The results obtained using the automated procedure are given below in Table 2 and are compared in Table 3, with results obtained by conventional techniques from which the bacteria are identified following the method of Cowan and Steel (1974 "Manual for the identification of Medical Bacteria" 2nd Edition, University Press, Cambridge).

TABLE 2

Distribution of positive results (%) in automated tests according to the invention

| | E. coli | Klebsiella spp | Proteus spp. | Pseudomonas spp. |
|---|---|---|---|---|
| No. strains | 125 | 39 | 16 | 19 |
| Automated tests | | | | |
| Acid phosphatase | 1 | 95 | 100 | 0 |
| Diacetyl/acetoin-producing (V-P) | 0 | 51 | 0 | 0 |
| $\beta$-galactosidase | 94 | 82 | 0 | 0 |
| Glutamate decarboxylase | 99 | 0 | 62 | 0 |
| Leucine deaminase | 0 | 8 | 94 | 0 |
| Cytochrome oxidase | 0 | 0 | 0 | 95 |
| Phenylalanine deaminase | 2 | 0 | 100 | 0 |
| Urease | 0 | 62 | 75 | 10 |

EXAMPLE 2

A total of 96 suspensions of different organisms is tested by the automated method described above in Example 1 and the preceding description, except in this case each suspension comprises a single colony of organisms in 1 ml of saline. The automated test procedure adopted is the same as in Example 1, though with fewer control runs, and similarly conventional tests are carried out on aliquots of each suspension for the sake of comparison. The results obtained, in terms of the success rate, are given below in Table 3 which also includes results for the success rate of the automated tests of Example 1.

TABLE 3

Agreement between automated and conventional identification

| | E. coli | Klebsiella spp. | Proteus spp. | Psuedomonas spp. | Total |
|---|---|---|---|---|---|
| No. of strains tested | | | | | |
| Example 1 | 125 | 39 | 16 | 19 | 199 |
| Example 2 Correct | 61 | 22 | 3 | 5 | 96 |

TABLE 3-continued

Agreement between automated and conventional identification

| | E. coli | Klebsiella spp. | Proteus spp. | Psuedomonas spp. | Total |
|---|---|---|---|---|---|
| identification by automated assay (%) | | | | | |
| Example 1 | 99 | 97 | 100 | 95 | 98 |
| Example 2 | 100 | 100 | 100 | 100 | 100 |

As can be seen, the agreement rate achieved with the automated system in Example 1 is 98%. The three strains that are not identified include a strain of Klebsiella spp. showing only acid phosphatase activity, a strain of E. coli showing only beta-galactosidase activity, and a strain of Pseudomonas spp. for which the cytochrome oxidase activity results are not available. All three organisms are originally classified as unidentified and on repeat testing are identified correctly. Thus, Table 3 indicates that it is possible to correctly identify all four bacterial groups, namely Escherichia, Klebsiella spp. and, Proteus spp., Pseudomonas spp., by the automated testing procedure.

The success rate achieved in Example 2 was as good as that in Example 1. Thus it is possible to identify some bacteria from a single colony by the above automated tests.

EXAMPLE 3

A total of 304 suspensions of culture collection and freshly isolated strains were tested by the full 26 test procedure of the invention as described below.

Culture collection strains were from the National Collection of Type Cultures, the Computer Trial Laboratory at Colindale and the Bacteriology Department, St. Mary's Hospital Medical School; all had been characterised and identified by conventional methods. Fresh strains were isolated from routine urine specimens and identified using API strip 20E. All strains were cultured overnight at 37° C. on MacConkey agar plates, without added sodium chloride (Difco Laboratory and Tissue Culture Services). Bacterial suspensions of 8 colonies in 4 ml sterile saline were used for all enzyme assays.

Figure 7:
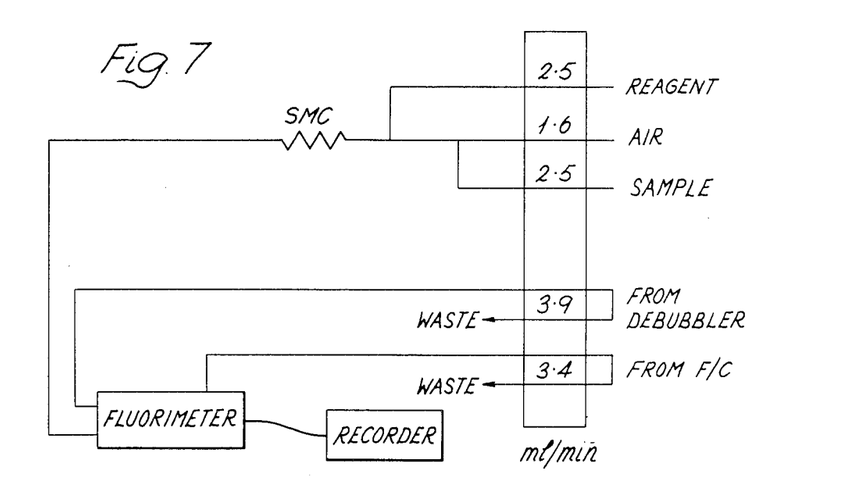

Enzyme activities were measured using 3 different analytical systems. The continuous flow system, as described in Example 1, was used to determine activity of cytochrome oxidase, glutamate decarboxylase and protein content. A semi-automated continuous flow method was used for detection of enzymes listed in Table 4, by fluorimetry using the continuous flow manifold shown in FIG. 7. A discrete analyser (Kem-O-Mat) was used to perform the tests listed in Table 5.

In the semi-automated method buffered substrate solution (200 μl) and bacterial suspension (200 μl) were added manually to Auto Analyzer cups. The bacteria and substrate mixture was incubated for 90 min. at 40° C. and the fluorescence measured in a Lochart fluorimeter attached to a Newton sampler, using a continuous flow manifold as detailed in FIG. 7. This system allowed measurement of 100 samples per hour. The enzymes tested and the composition of the reagents are given in Tables 4(a) and 4(b).

TABLE 4(a)

| | | Hydrolases | | |
|---|---|---|---|---|
| | | Buffered substrate | | |
| Enzyme | Buffer | Substrate | Concn. mM | Manifold reagent |
| Lipase | Tris-HCl pH 9.0, 0.05 M | 4-methylumbelliferyl-nonanoate | 0.05 | HCl 20 mM |
| α-Glucosidase | Tris phosphate pH 8.0, 0.1 M | 4-methylumbelliferyl-α-D-glucopyranoside | 0.2 | HCl 20 mM |
| β-Glucosidase | Tris phosphate pH 2.0, 0.1 M | 4-methylumbelliferyl-β-D-glucopyranoside | 0.5 | HCl, 20 mM |
| β-Xylosidase | Tris phosphate pH 8.0, 0.1 M | 4-methylumbelliferyl-β-D-xylopyranoside | 0.2 | HCl, 20 mM |
| β-Glucuronidase | sodium acetate pH 5.6, 0.1 M | 4-methylumbelliferyl-β-D-glucuronide | 0.5 | glycine buffer pH 8.8, 1 mM |

All substrates were supplied by Koch Light. They were dissolved in methoxyethanol and diluted with appropriate buffer to the final concentrations listed.

TABLE 4(b)

Substrates used for peptidase assays

| Substrate | Supplier |
|---|---|
| DL-Alanine-β-naphthylamide hydrochloride | Sigma |
| L-Arginine-β-naphthylamide hydrochloride (arg-NAP) | Sigma |
| N—γ-L-Glutamyl-β-naphthylamide | Sigma |
| Glycyl-β-naphthylamide hydrochloride | Koch Light |
| L-4-Hydroxyprolyl-β-naphthylamide (OH—pro-NAP) | Sigma |
| L-Leucyl-β-naphthylamide hydrochloride (leu-NAP) | Sigma |
| L-Leucyl-4-methoxy-β-naphthylamide hydrochloride (leu-4-m-NAP) | Sigma |
| L-Lysyl-β-naphthylamide carbonate | Koch Light |
| L-Prolyl-β-naphthylamide hydrochloride (pro-NAP) | Sigma |
| L-Pyrrolidonyl-β-naphthylamide (pyr-NAP) | Sigma |

All substrates were dissolved in dimethyl sulphoxide and diluted to a final substrate concentration of 0.1 mM with 0.1M Tris phosphate buffer, pH 8.0, containing cabaltous nitrate (2 μM). The reagent used in the continuous flow manifold was 0.1M Tris phosphate buffer, pH 8.0.

The discrete analyser, Kem-O-Mat, (Coulter Electronics) was used to perform the tests listed in Table 5. The bacterial suspensions were placed in the sample cups, buffers were dispensed by the diluent syringe, substrates and reagents (for developing the colour of the reaction end-products) were dispensed by the reagent syringe. To increase sample throughput and lengthen incubation periods, cuvettes containing bacterial suspensions, buffer and substrate were incubated outside the Kem-O-Mat. The cuvette changer was used for simultaneous insertion of all 32 cuvettes and for their removal. Two program cartridges were used to perform each test. Program cartridge 1 was used for distribution of bacterial suspensions, buffer, cofactors and substrate to each cuvette and for reading the initial absorbance of each cuvette. The cuvettes were then removed and placed in a 40° C. incubator. The diluent and reagent syringes and probes were rinsed and charged with the reagents for the next enzyme test. After incubation the cuvettes of each enzyme test were returned to the analyser. Program cartridge 2 was used for adding the second reagent and for reading the final absorbance. The details of reagent composition are given in Table 5. For all tests 350 μl of diluent and 70 μl of reagent 1 were dispensed into each cuvette. Bacterial suspensions were dispensed in 50 μl aliquots for the DNAase test and in 25 μl aliquots for all other tests. Minimum incubation periods for tryptophanase and DNAase were 2 h, for VP and PNPA 1½ h, and for the remaining tests one hour. At the end of the incubation period reagent 2 was added to the cuvettes containing substrate and bacterial suspension in 50 μl aliquots for the VP, PNPA, PNPP, PNPP+C+L and PNPG+C+L tests and in 350 μl aliquots for the INDOLE test. Final absorbance was read 2 min after addition of the second reagent, except for VP and INDOLE tests which were read after 20 min. Absorbance measurements from the 3 different analytical systems were fed into a computer for calculation of enzyme activity and specific enzyme activity of each organism suspension in each enzyme test.

flow systems on a total of 26 tests and a protein assay. Thirty one strains were excluded from the calculations because of missing values, mixed cultures and doubtful identity by conventional testing. The remaining 273 cultures were divided into a known set (Training Set) comprising of between 210 and 221 cultures of mainly culture collection strains; and an unknown set (Test Set) of 52-73 cultures, mainly of strains freshly isolated from cultured urine specimens and tested the day after the urine specimen was received.

The discriminant function analysis (DFA) using SPSS software was used to identify both training and test sets.

The 35 species were divided either into 17 genera or sub-divided within each genus to species or groups of species as shown in Table 6.

TABLE 6

Division and coding of bacterial taxa in discriminant function analysis (DFA)

| Bacterial taxon | Coding used in DFA Number of groups | | | | | |
|---|---|---|---|---|---|---|
| | 17 | 22A | 22B | 25A | 25B | 35 |
| Escherichia | 1 | 1 | 1,2 | 1,2 | 1,2 | 1 |
| Klebsiella pneumoniae sensu lato | 2 | 2 | 3 | 3 | 3 | 2 |
| Klebsiella rhinoschleromatis | 2 | 2 | 3 | 4 | 4 | 3 |
| Klebsiella oxytocum | 2 | 2 | 3 | 3 | 3 | 4 |
| Proteus mirabilis | 3 | 3 | 4 | 5 | 5 | 5 |
| Proteus morganii | 3 | 3 | 4 | 6 | 6 | 6 |
| Proteus rettgeri | 3 | 0 | 0 | 0 | 0 | 7 |
| Proteus vulgaris | 3 | 3 | 4 | 7 | 7 | 8 |
| Pseudomonas aeruginosa | 4 | 4 | 5 | 8 | 8 | 9 |
| Pseudomonas cepacia | 4 | 5 | 6 | 9 | 9 | 10 |
| Pseudomonas fluorescens | 4 | 6 | 7 | 8 | 8 | 11 |
| Staphylococcus epidermidis | 5 | 7 | 8 | 11 | 11 | 12 |

TABLE 5

| Test | Diluent* | Reagent 1 | Reagent 2 |
|---|---|---|---|
| Diacetyl/acetoin producing enzymes (V-P reaction) (VP) | 0.05 M acetate buffer, pH 4.5, containing 0.15 M sodium pyruvate, creatine 1 g/l and NaCl, 4.25 g/l | 0.4 mM cocarboxylase | 2 M NaOH containing α-naphthol 50 g/l |
| p-Nitrophenylalanine ammonia-lyase (PNPA) | 0.1 M potassium phosphate buffer, pH 8.0 | 10 mM DL-β-(p-nitrophenyl) alanine | 1.9 M ammonium hydroxide containing 0.68 M NaOH and Triton-X-100, 0.3 g/l |
| Alanyl-p-nitroaniline specific peptidase (PNAA) | 0.1 M potassium phosphate buffer, pH 8.0 | 3.5 mM L-alanine-4-nitroanilide hydrochloride (BDH) | — |
| Glutamyl-p-nitroaniline specific peptidase (PNAG) | 0.07 M Tris-phosphate buffer, pH 8.0, containing cobaltous nitrate 2 μM | 3.5 mM γ-L-glutamyl 4-nitroanilide | — |
| Acid phosphatase (PNPP) | 0.03 M sodium acetate buffer, pH 5.6, containing NaCl, 2.8 g/l | 5 mM p-nitrophenyl-disodium phosphate | 1.9 M ammonium hydroxide containing 0.68 M NaOH and Triton-X-100, 0.3 g/l |
| Acid phosphatase (PNPP + C + L) | 0.03 M sodium acetate buffer pH 5.6, containing cetrimide, 0.007 g/l; lysozyme, 0.007 g/l; and NaCl, 2.8 g/l | 5 mM p-nitrophenyl-disodium phosphate | 1.9 M ammonium hydroxide containing 0.68 M NaOH and Triton-X-100, 0.3 g/l |
| β-Galactosidase (PNPG + C + L) | 0.03 M potassium phosphate buffer, pH .5, containing cetrimide, 0.007 g/l; lysozyme, 0.007 g/l; and NaCl, 2.8 g/l | 8 mM p-nitrophenyl-β-D-galactopyranoside | 1.9 M ammonium hydroxide containing 0.68 M NaOH and Triton-X-100, 0.3 g/l |
| Tryptophanase (INDOLE) | Peptone (Oxoid L37) 5 g/l and NaCl 6.75 g/l in distilled water | 2 mM L-tryptophan | 78% (v/v) ethanol containing 1.16 M HCl and p-dimethyl-aminocinnamaldehyde, 2.37 g/l |
| Deoxyribonuclease (DNA) | 0.07 M Tris-HCl buffer, pH 9.0, containing MgCl$_2$ 20 mM; ethidium bromide; 23 mg/l, and deoxyribonucleic acid (Sigma calf thymus), 227 mg/l | distilled water | — |

*All diluent solutions contain Triton-X-100, 0.1 ml/l, to decrease air bubbles on cuvette walls.

Analysis of results

Three hundred and four cultures falling into 35 species were tested by both Kem-O-Mat and continuous TABLE 6-continued Division and coding of bacterial taxa in discriminant function analysis (DFA)

| Bacterial taxon | Coding used in DFA Number of groups | | | | | |
|---|---|---|---|---|---|---|
| | 17 | 22A | 22B | 25A | 25B | 35 |
| Staphylococcus aureus | 5 | 7 | 8 | 10 | 10 | 13 |
| Staphylococcus saprophyticus | 5 | 7 | 8 | 11 | 11 | 14 |
| Streptococcus | 6 | 8 | 9 | 12 | 12 | 15 |
| Citrobacter freundii | 7 | 9 | 10 | 13 | 13 | 16 |
| Citrobacter koseri | 7 | 10 | 11 | 14 | 14 | 17 |
| Providencia alkalifaciens | 8 | 11 | 12 | 15 | 15 | 18 |
| Providencia stuartii | 8 | 11 | 12 | 15 | 15 | 19 |
| Serratia marcescens | 9 | 12 | 13 | 16 | 16 | 20 |
| Serratia rubidaea | 9 | 12 | 13 | 16 | 16 | 21 |
| Serratia liquefaciens | 9 | 12 | 0 | 16 | 0 | 22 |
| Acinetobacter calcoaceticus va. anitratus | 10 | 13 | 14 | 17 | 17 | 23 |
| Acinetobacter calcoaceticus va. lwoffi | 10 | 13 | 14 | 17 | 17 | 24 |
| Alcaligenes faecalis | 11 | 14 | 15 | 18 | 18 | 25 |
| Alcaligenes bronchisepticus | 11 | 15 | 16 | 19 | 19 | 26 |
| Flavobacterrium meningosepticum | 12 | 16 | 17 | 20 | 20 | 27 |
| Enterobacter aerogenes | 13 | 17 | 18 | 21 | 21 | 28 |
| Enterobacter cloacae | 13 | 18 | 19 | 22 | 22 | 29 |
| Enterobacter agglomerans | 13 | 17 | 18 | 21 | 21 | 30 |
| Hafnia alvei | 14 | 19 | 20 | 23 | 23 | 31 |
| Salmonella | 15 | 20 | 0 | 0 | 0 | 32 |
| Edwardsiella tarda | 16 | 21 | 21 | 24 | 24 | 33 |
| Aeromonas hudrophila | 17 | 22 | 22 | 25 | 25 | 34 |
| Aeromonas formicans | 17 | 22 | 22 | 25 | 25 | 35 |

Each grouping was subjected to DFA using all 26 tests (variables) and a number of restricted sets of variables, to determine the best mathematical treatment of the data.

The percentage agreements with previous identification obtained with the Training and Test Sets in the various combinations are shown in Table 7 when all 26 variables were included.

TABLE 7

Effect of grouping of taxa in the DFA on identification performance using all 26 variables

| | Training Set | | Test set | |
|---|---|---|---|---|
| No. of groups | No. of strains | Agreement % | No. of strains | Agreement % |
| 17 | 215 | 74.5 | 64 | 45.2 |
| 22A | 215 | 78.9 | 64 | 45.9 |
| 22B | 215 | 80.9 | 68 | 47.2 |
| 25A | 221 | 81.4 | 52 | 50.0 |
| 25B | 215 | 82.3 | 58 | 48.3 |
| 35 | 215 | 70.3 | 64 | 56.9 |

Highest percent of agreement was obtained in the training set with the 25B grouping and with the test set with 25A grouping. The effect on agreement percentage of exclusion of selected variables from the DFA is shown in Tables 8 and 9, using 22B and 25B groupings.

TABLE 8

Effect of excluding selected variables in the DFA on identification performance, using 22B grouping

| No. of variables | Agreement % | Variables excluded, in addition to those excluded in the preceding line |
|---|---|---|
| 26 | 80.9 | — |
| 25 | 81.4 | PNAG |
| 24 | 80.5 | VP |
| 23 | 75.8 | INDOLE |
| 22 | 76.3 | PNAA |
| 21 | 74.4 | Glutamate decarboxylase |
| 20 | 73.0 | PNPA |
| 15 | 67.4 | Arg-NAP, leu-NAP, pro-NAP, β-glucuronidase, DNAase |
| 10 | 51.2 | OH—pro-NAP, leu-4-m-NAP, pyr-NAP, α-glucosidase, β-glucosidase |

TABLE 9(a)

Effect of excluding selected variables in the DFA on identification performance, using 25B grouping

| Number of strains | Bacterial genus | Number of Variables | | | | |
|---|---|---|---|---|---|---|
| | | 26 | 25 | 24 | 23 | 23 |
| | | % Agreement | | | | |
| 23 | Escherichia | 95.6 | 91.3 | 91.3 | 91.3 | 91.3 |
| 24 | Klebsiella | 87.5 | 87.5 | 87.5 | 87.5 | 83.3 |
| 26 | Proteus | 69.2 | 65.4 | 65.4 | 65.4 | 65.4 |
| 17 | Pseudomonas | 94.1 | 94.1 | 94.1 | 94.1 | 94.1 |
| 19 | Staphylococcus | 84.2 | 84.2 | 78.9 | 78.9 | 78.9 |
| 7 | Streptococcus | 85.7 | 85.7 | 85.7 | 85.7 | 85.7 |
| 13 | Citrobacter | 84.6 | 84.6 | 84.6 | 84.6 | 84.6 |
| 17 | Providencia | 94.2 | 94.2 | 94.2 | 82.3 | 94.2 |
| 21 | Serratia | 71.4 | 71.4 | 71.4 | 66.6 | 61.9 |
| 10 | Acinetobacter | 70.0 | 80.0 | 70.0 | 70.0 | 60.0 |
| 7 | Alcaligenes | 100 | 100 | 100 | 100 | 100 |
| 2 | Flavobacterium | 100 | 100 | 100 | 100 | 100 |
| 22 | Enterobacter | 68.2 | 68.2 | 63.6 | 63.6 | 63.6 |
| 5 | Hafnia | 100 | 100 | 100 | 100 | 100 |
| 6 | Edwardsiella | 100 | 100 | 100 | 100 | 100 |
| 9 | Aeromonas | 77.8 | 77.8 | 77.8 | 77.8 | 77.8 |
| | All genera | 83.8 | 84.8 | 82.0 | 81.4 | 81.0 |
| 228 | Tests excluded | NONE | PNAG | PNAG VP | PNAG VP PNPA | PNAG α-glucosidase β-xylosidase |

TABLE 9(b)

Effect of number of tests on % agreement with conventional identification

| Percentage agreement | Number of variables | | | | |
|---|---|---|---|---|---|
| | 26 | 25 | 24 | 23 | 23 |
| | Number of genera in each category | | | | |
| 90–100 | 7 | 7 | 7 | 6 | 7 |
| 80–89.9 | 4 | 5 | 3 | 3 | 3 |
| 70–79.9 | 3 | 2 | 4 | 3 | 2 |

TABLE 9(b)-continued

| Effect of number of tests on % agreement with conventional identification | | | | | |
|---|---|---|---|---|---|
| | Number of variables | | | | |
| Percentage agreement | 26 | 25 | 24 | 23 | 23 |
| | Number of genera in each category | | | | |
| 60–69.9 | 2 | 2 | 2 | 3 | 4 |

In both cases exclusion of the PNAG test results in a slight increase in the total percentage agreement as well as in the number of genera showing 80% agreement. It is believed that this was due to experimental inaccuracies in the results arising from the PNAG test. Exclusion of further tests whether by computer selection or by inspection causes further decrease in the % of agreement which is unacceptable.

The taxa which proved difficult to separate are *Proteus rettgeri, Acinetobacter anitratus,* and the Enterobacter/Serratia species. This is probably a result of use of strains kept for a long time in culture.

Some of these strains when tested by both the conventional API 20 and R/B tube kits did not show 'good identification' and in a number of strains the results of one system did not agree with those of the second.

More strains, preferably freshly isolated ones, are needed for solving the difficulties in these taxa.

The results obtained show, however, that the full procedure of the invention gives greater than 80% accuracy of identification over a very wide range of different bacteria. It is believed that this accuracy can be increased if enzyme profile information from a large and more representative group of previously identified bacteria is available for comparison.

I claim:

1. In a procedure for use in the identification of bacteria, in which a bacterial sample to be identified is subjected to a combination of tests in which the sample is incubated with substrates for bacterial enzymes and the bacterial enzymes of the sample are determined by their interaction with the substrate to give rise to a detectable product, the improvement which comprises a quantitative determination of constitutive enzymes without depending on the growth of the bacteria, except in the case of tryptophanase and deoxyribonuclease, which require additional time, and comparing the results of the tests with a predetermined standard to identify bacterial species, using all of the following enzymes (a)–(z) in the test:
   (a) lipase
   (b) alpha-glucosidase
   (c) beta-glucosidase
   (d) beta-xylosidase
   (e) beta-glucuronidase
   (f) beta-galactosidase
   (g) whole cell acid phosphatase
   (h) acid phosphatase in the presence of agents which disrupt the bacterial cell permeability barrier
   (i) DL-alanyl-beta-naphthylamine specific peptidase
   (j) L-arginyl-beta-naphthylamine specific peptidase
   (k) N-gamma-L-glutamyl-beta-naphthylamine specific peptidase
   (l) glycyl-beta-naphthylamine specific peptidase
   (m) L-4-hydroxyprolyl-beta-naphthylamine specific peptidase
   (n) L-leucyl-beta-naphthylamine specific peptidase
   (o) L-leucyl-4-methoxy-beta-naphthylamine specific peptidase
   (p) L-lysyl-beta-naphthylamine specific peptidase
   (q) L-prolyl-beta-naphthylamine specific peptidase
   (r) L-pyrrolidonyl-beta-naphthylamine specific peptidase
   (s) alanyl-p-nitroaniline specific peptidase
   (t) glutamyl-p-nitroaniline specific peptidase
   (u) diacetyl/acetoin-producing enzymes
   (v) p-nitrophenylalanine ammonia-lyase
   (w) tryptophanase
   (x) deoxyribonuclease
   (y) glutamate decarboxylase
   (z) cytochrome oxidase.

2. The procedure according to claim 1, characterised in that the period of incubation is from about 10 minutes up to about 2 hours except for the tryptophanase and deoxyribonuclease tests (w) and (x).

3. The procedure according to claim 1, characterised in that the tryptophanase and deoxyribonuclease tests (w) and (x) are carried out with a period of incubation of 2 to 2½ hours.

4. The procedure according to claim 2, characterised in that the tryptophanase and deoxyribonuclease tests (w) and (x) are carried out with a period of incubation of 2 to 2½ hours.

5. The procedure according to claim 1, characterised in that the procedure is carried out on a sample derived from a single colony of bacteria produced by pre-culture of a clinical specimen.

6. The procedure according to claim 2, characterised in that the procedure is carried out on a sample derived from a single colony of bacteria produced by pre-culture of a clinical specimen.

7. The procedure according to claim 1, characterised in that a single procedure, using only the defined combination of tests, is used for identification of the bacterial sample.

8. The procedure according to claim 2, characterised in that a single procedure, using only the defined combination of tests, is used for identification of the bacterial sample.

9. A kit comprising reagents for use in a procedure according to claim 1, characterised by comprising separate specific substrates for each of the enzymes defined in claim 1.

10. The kit according to claim 9, characterised in that the enzyme substrates give rise to products which may be measured by fluorimetry or colorimetry.

11. The kit according to claim 10, characterised in that said kit includes colour-developing or fluorescence-developing reagent(s).

* * * * *